United States Patent
Pallares et al.

(10) Patent No.: US 12,295,911 B2
(45) Date of Patent: May 13, 2025

(54) PORT, DISPENSING SYSTEM COMPRISING SUCH A PORT, AND MANUFACTURING METHOD

(71) Applicant: SARTORIUS STEDIM FMT SAS, Aubagne (FR)

(72) Inventors: Alain Pallares, La Bouilladisse (FR); Ali Barhoumi, Mhamdia Ben Arous (TN); Marie-Christine Menier, La Ciotat (FR)

(73) Assignee: SARTORIUS STEDIM FMT, Aubagne (FR)

( * ) Notice: Subject to any disclaimer, the term of this patent is extended or adjusted under 35 U.S.C. 154(b) by 1212 days.

(21) Appl. No.: 16/090,433

(22) PCT Filed: Mar. 30, 2017

(86) PCT No.: PCT/FR2017/050729
§ 371 (c)(1),
(2) Date: Oct. 1, 2018

(87) PCT Pub. No.: WO2017/168097
PCT Pub. Date: Oct. 5, 2017

(65) Prior Publication Data
US 2019/0117510 A1   Apr. 25, 2019

(30) Foreign Application Priority Data
Mar. 31, 2016 (FR) .................................. 16 52766

(51) Int. Cl.
*A61J 1/10* (2006.01)
*A61J 1/14* (2023.01)
(Continued)

(52) U.S. Cl.
CPC ............... *A61J 1/1406* (2013.01); *A61J 1/10* (2013.01); *A61J 1/1412* (2013.01); *A61J 1/1468* (2015.05);
(Continued)

(58) Field of Classification Search
CPC .......... A61J 1/10; A61J 1/1406; A61J 1/1412; A61J 1/1468; A61J 1/1475; A61J 1/1481; A61J 1/2096; A61M 39/00; A61M 39/04
See application file for complete search history.

(56) References Cited

U.S. PATENT DOCUMENTS 3,030,955 A   4/1962   Gossett et al.
4,303,067 A   12/1981   Connolly et al.
(Continued)

FOREIGN PATENT DOCUMENTS

| FR | 2665633 | * | 2/1992 |
| GB | 928 842 | | 6/1963 |
| WO | WO 2015/061711 | | 4/2015 |

OTHER PUBLICATIONS

International Search Report, PCT/FR2017/050729, dated Jul. 3, 2017.

*Primary Examiner* — Kai H Weng
(74) *Attorney, Agent, or Firm* — NIXON & VANDERHYE

(57) ABSTRACT

A port is suitable for attachment to a container and suitable for being traversed by a needle used to transfer content between the inside of the container and the outside of the container, and includes a rigid annular body extending in a direction including a side wall surrounding a channel extending between an inner end and an outer end, the inner and outer ends being at opposite ends along the direction, the body being open at the ends, an overmolding member of thermoplastic elastomer including a sealing portion suitable for being traversed by the needle in a direction close to the (Continued)

direction, the needle passing through the inner and outer ends, the overmolding member sealing the channel in a fluidtight manner after withdrawal of a needle and further including an adhesion portion suitable for attaching the port to the container.

18 Claims, 5 Drawing Sheets

(51) Int. Cl.

| | | |
|---|---|---|
| *A61J 1/20* | (2006.01) | |
| *A61M 39/00* | (2006.01) | |
| *A61M 39/04* | (2006.01) | |
| *B29C 70/68* | (2006.01) | |
| *B29L 31/00* | (2006.01) | |

(52) U.S. Cl.
CPC ............ *A61J 1/1475* (2013.01); *A61J 1/1481* (2015.05); *A61J 1/2096* (2013.01); *A61M 39/00* (2013.01); *A61M 39/04* (2013.01); *B29C 70/68* (2013.01); *B29L 2031/753* (2013.01)

(56) References Cited

U.S. PATENT DOCUMENTS

| | | | | |
|---|---|---|---|---|
| 5,342,319 | A * | 8/1994 | Watson | A61M 5/00 604/167.02 |
| 2010/0179505 | A1* | 7/2010 | Muramatsu | A61J 1/1475 156/290 |
| 2011/0144596 | A1* | 6/2011 | Kobashi | B65D 25/48 604/257 |
| 2012/0284991 | A1* | 11/2012 | Kusz | A61M 39/12 137/315.01 |
| 2013/0237946 | A1* | 9/2013 | Lynn | A61J 1/1487 604/414 |
| 2014/0008366 | A1* | 1/2014 | Genosar | A61J 1/2096 220/265 |
| 2014/0126843 | A1* | 5/2014 | Mochizuki | A61J 1/1493 53/425 |
| 2014/0174578 | A1* | 6/2014 | Bonnal | A61M 39/26 137/798 |
| 2014/0276649 | A1* | 9/2014 | Ivosevic | A61J 1/2096 604/533 |
| 2015/0013837 | A1* | 1/2015 | Barrelle | A61J 1/2096 141/330 |

\* cited by examiner

PORT, DISPENSING SYSTEM COMPRISING SUCH A PORT, AND MANUFACTURING METHOD

BACKGROUND OF THE INVENTION

Field of the Invention

The invention relates to ports, dispensing systems comprising such ports, and their manufacturing methods.

More specifically, the invention relates to a port suitable for attachment to a container and suitable for being traversed by a needle used to transfer content between the inside of the container and the outside of the container, in the biopharmaceutical and medical field.

Description of the Related Art

In the past, to transfer a fluid between the inside and the outside of a container by means of a needle, a port made of polymer was used (such as polycarbonate or acrylonitrile butadiene styrene ABS), equipped with a septum made of silicone for example obstructing one of the ends of the port, such as described in the commercial brochure for products in the "total parenteral nutrition pouch" line available from Sartorius. In this case, the needle passes through the port, in particular the septum, and the port is glued to the container.

As the polymer used for the port generally cannot be directly attached by welding to the film of the container (pouch of ethylene vinyl acetate EVA), it is necessary to use a short polyethylene tube into which the port is inserted. The port is attached to the tube by gluing using a cyanoacrylate glue, and the outer wall of the tube is welded to the wall of the container.

As the polyethylene used for the tubes is a difficult material to glue to, the attachment between tube and port is therefore ineffective, which causes durability issues for the assembly and therefore potential leakage problems if the gluing is ineffective. In particular, there is a risk of tearing the port off the tube when the needle is withdrawn. The use of glue also poses toxicity issues and a risk of contamination of the assembly if the adhesion process is not carried out correctly, which is particularly troublesome if all chemical and/or particulate contamination of the contents of the container must absolutely be avoided.

There is therefore a need to develop an alternative means for attaching a port, intended for a needle, to a container for biopharmaceutical applications as well as for medical devices.

BRIEF SUMMARY OF THE INVENTION

For this purpose, the port according to this invention is such that it comprises: a rigid annular body extending in a direction, said body comprising a side wall surrounding a channel extending between an outer end and an inner end, said outer and inner ends being at opposite ends along said direction, said body being open at said inner and outer ends; and an overmolding member of thermoplastic elastomer, the overmolding member comprising a sealing portion adapted to be traversed by the needle in a direction close to said direction, the needle passing through the inner and outer ends in order to transfer content between the inside and the outside by means of the needle, the overmolding member sealing the channel in a fluidtight manner in the absence of a needle after withdrawal of the needle, the overmolding member further comprising an adhesion portion suitable for attaching the port to the container.

In this case, the port can be welded directly to a container, significantly improving the strength and fluidtightness of the port with the container for the transfer of medical or biopharmaceutical fluid, and reducing the risk of contamination.

In addition, the needle passes through the sealing portion when the latter is contained within the container, which restricts the path of the needle and reduces the risk of the needle tip piercing the container.

Because the thermoplastic elastomer constituting the overmolding member has a memory effect, after passage of the needle and its withdrawal during use, the pore opened in the overmolding member by the passage of the needle closes up again, the product contained in the container thus being retained in a container which has once again become fluidtight after removal of the needle, eliminating any risk of contamination via the created pore.

In the case of ports as described in the Sartorius commercial brochure, the containers are usually tested for integrity by placing them under pressure with said tube assembled and sealed, in other words without a port. A port is then glued to each tested container, but fluidtightness with the glued port is not tested. In the case of the invention, the container will be tested with the port already welded, which increases reliability for the user of the product.

According to some aspects, one or more of the following arrangements may be used:
- the rigid body is made of a thermoplastic polymer selected among polypropylene and high-density polyethylene;
- the rigid body comprises ribs formed in the thickness of the wall, an outer portion of said body extending continuously from the inner end of said body, said ribs being of elongate shape and oriented in a direction substantially parallel to direction X, said ribs being formed in the outer portion of the body;
- the ribs either extend in a straight line or zigzag along direction X;
- the rigid body comprises a cap member, the cap member having dimensions suitable for sealing the outer end of the body;
- the cap member is connected to the rigid body by a connector, the cap member, rigid body, and connector being molded as one piece;
- the rigid body comprises an additional element forming a breakable portion, said breakable portion comprising an outer end and an inner end, the breakable portion extending in direction X from the outer end of the rigid body so as to define a connection region in the area where the outer end of the body meets the inner end of the breakable portion, the outer end of the breakable portion being sealed closed;
- the rigid body is molded, said body being weakened at the connection region;
- the breakable portion comprises fins suitable for gripping in order to detach the breakable portion from the rigid body;
- said fins are molded with the breakable portion.

According to a second aspect, an object of the invention is a system for dispensing content between the inside of a container and the outside of a container by means of a needle, in the biopharmaceutical and medical field, said system comprising such a port and a container, said container comprising a wall with an opening in its wall, the overmolding member being partially inserted into the container through the opening, the wall of the container at its opening being welded to the adhesion portion of the overmolding member.

In particular, the dispensing system is such that the container is a flexible pouch of plastic film for holding biopharmaceutical content or for a medical device, and more particularly a disposable flexible pouch, and even more particularly a disposable flexible pouch having a layer in contact with the biopharmaceutical fluid that is composed of EVA (ethylene vinyl acetate).

According to a third aspect, an object of the invention is a method for manufacturing a port suitable for attachment to a container and suitable for being traversed by a needle used to transfer content between the inside of the container and the outside of the container, in the biopharmaceutical and medical field, wherein there is provided: a rigid annular body extending in a direction, said body comprising a side wall surrounding a channel extending between an inner end and an outer end, said outer and inner ends being at opposite ends along said direction, said body being open at said inner and outer ends, an outer portion of said body extending continuously from the inner end of said body; a system of molds, suitable for the manufacture of an overmolding member of thermoplastic elastomer; and a molding product; the manufacturing method comprising the following steps: placing the system of molds so as to enable the manufacture of an overmolding member comprising a sealing portion suitable for being traversed by the needle in a direction close to said direction, the needle passing through the inner and outer ends in order to transfer content between the inside and the outside by means of the needle, the overmolding member sealing the channel in a fluidtight manner in the absence of a needle after withdrawal of the needle, the overmolding member further comprising an adhesion portion suitable for attaching the port to the container; molding said overmolding member; and then removing the mold system.

In particular, the method for manufacturing a port via the technique of overmolding by transfer is such that:
the system of molds comprises two molds, a first mold suitable for enveloping the outer portion of said body and a second mold suitable for insertion into the rigid body, the molding step consisting of pouring the molding product between the first and second molds;
the body (10) is obtained during a prior molding step.

According to a fourth aspect, an object of the invention is a method for manufacturing a system for dispensing content between the inside of a container and the outside of a container by means of a needle, in the biopharmaceutical and medical field, for which are provided a port, a container, said container comprising a wall with an opening in its wall, the method comprising a step such that the overmolding member is partially inserted into the container through the opening, the wall of the container at its opening being welded by high frequency welding to the adhesion portion of the overmolding member by applying an electromagnetic field through the rigid body.

BRIEF DESCRIPTION OF THE DRAWINGS

The figures of the drawings are now briefly described.

DETAILED DESCRIPTION OF THE PREFERRED EMBODIMENTS

Below is a detailed description of several embodiments of the invention, with examples and with reference to the figures.

Figure 1:
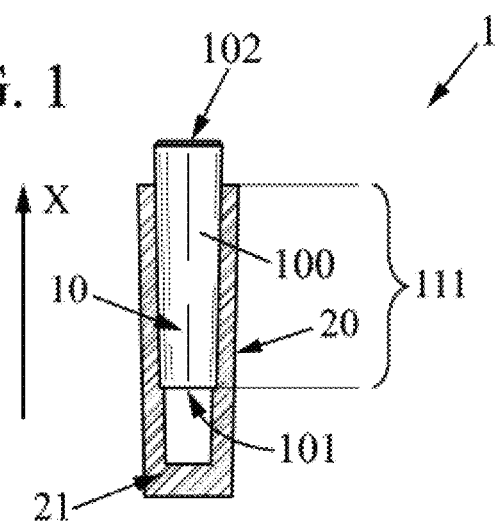
FIG. 1 is a side view, partially in section, illustrating a port.

FIG. 1 illustrates a port 1 comprising a rigid annular body 10 extending in a direction X, said body 10 comprising a side wall 100 surrounding a channel extending between an inner end 101 and an outer end 102, said inner and outer ends 101, 102 being at opposite ends along direction X, said body being open at said inner and outer ends 101, 102. In the case where a needle is received by the port, it will be oriented in a direction close to direction X and passing through each of said ends 101 and 102.

The port 1 also comprises an overmolding member 20 made of thermoplastic elastomer.

The overmolding member 20 comprises a sealing portion 21 adapted to be traversed by the needle in a direction close to direction X, the needle passing through the inner and outer ends 101, 102 to enable the transfer of content between the inside and the outside by means of the needle. The overmolding member seals the channel closed in the absence of a needle after withdrawal of the needle.

The overmolding member furthermore comprises an adhesion portion adapted for attaching the port to the container. The overmolding 20 is for example an annular body extending in direction X and closed at one of its ends by its sealing portion 21. The overmolding extends around the body 10 and comprises an inner surface and an outer surface, such that the inner surface of the overmolding 20 is in contact with the side wall 100 of the rigid body 10, on an outer portion 111 of said body extending continuously from the inner end 101 of said body 10. The annular body which constitutes the overmolding extends continuously beyond the inner end 101 of the body 10, and is closed off by its sealing portion 21, such that its sealing portion is opposite the open inner end 101, a space being left free between the sealing portion 21 of the overmolding 20 and the inner end 101 of the body 10. The adhesion portion of the overmolding is therefore at the outer surface of the overmolding.

Figure 2:
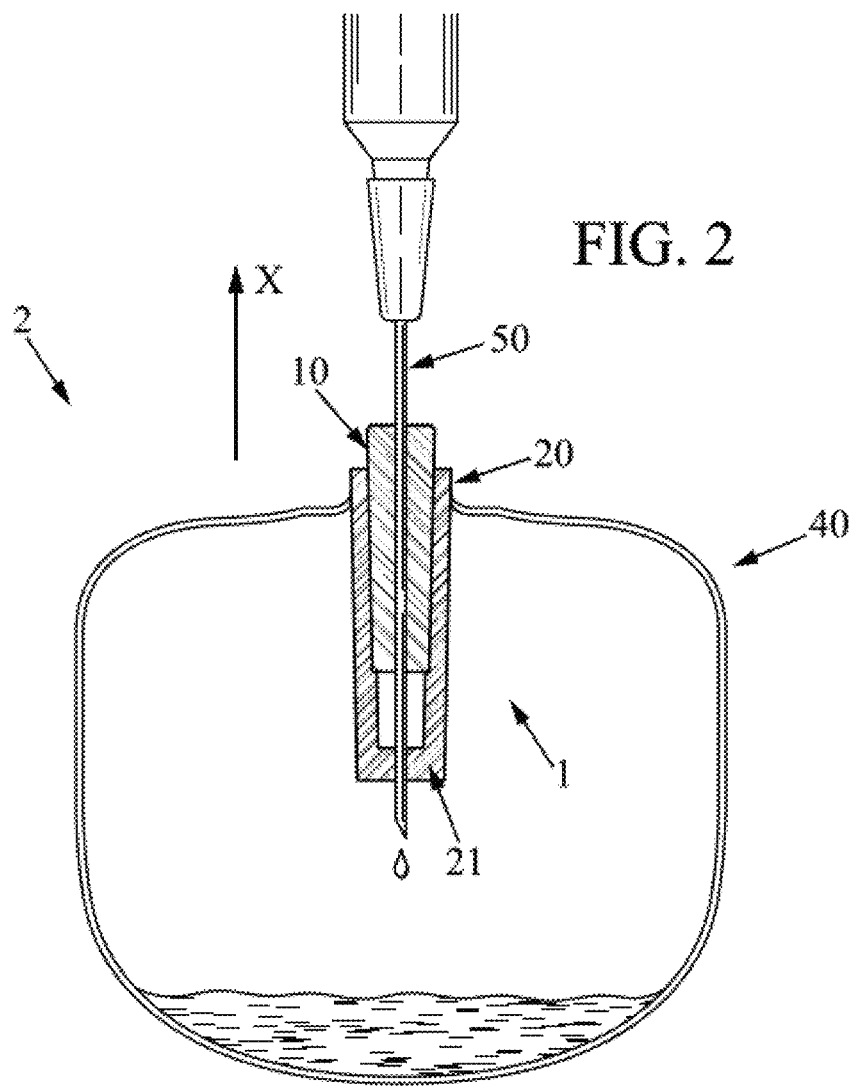
FIG. 2 is a side view, partially in section, illustrating a dispensing system.

During use, to allow the transfer of content between the inside of the container 40 and the outside of the container 40, in the biopharmaceutical and medical field, by means of a needle 50 through such a port 1, said container 40 will be welded directly to the port 1 traversable by the needle used for the transfer, the assembly of container and port forming a dispensing system 2. More precisely, the container 40 may for example be a flexible pouch with a wall having an opening reserved in its wall. As illustrated in FIG. 2, the overmolding member 20 will be partially inserted into the pouch 40 through its opening and the wall of the pouch at its opening will be welded at the adhesion portion of the overmolding member 20. In the example represented, the port 1 is shown assembled onto the inner portion of the wall of the pouch, such that the inner end 101 of the body 10 is an end inside the pouch, and the outer end 102 is an end outside the pouch. Alternatively, the port may be assembled to the pouch near the sealing portion 21 of the port, such that the inner end 101 of the body 10 is an end outside the pouch and the outer end 102 is an end outside the pouch.

Thus, in the case where the port 1 will receive a needle 50, the needle 50 will traverse the portion of the overmolding member 20 which envelopes the inner end 101, called the septum region 21 or sealing portion, so that the contents of the needle (or of a syringe) can be transferred into the pouch through the needle. The port 1 may in particular be used for inserting the needle of a syringe, to add products via a syringe to a mixture initially contained in the pouch 40. It will also be possible to use the port 1 for inserting a needle of a syringe in order to collect some of the contents of the pouch.

More specifically, the overmolding member 20 is made of thermoplastic elastomer. The choice of such a material, which has a memory effect, means that during use, after the passage of the needle through the sealing portion and its withdrawal, the pore opened in the overmolding member 20 by the passage of the needle closes, eliminating any risk of contamination.

In addition, the choice of a thermoplastic elastomer for the overmolding member 20 will facilitate the welding of a pouch 40 of plastic film to the overmolding 20.

In particular, a pouch of EVA film (ethylene vinyl acetate) suitable for containing blood products and bio-drugs may be used. Such a material for the pouch, which is easily welded to the overmolding member 20, gives great flexibility to the pouch 40. Such a pouch can also be sterilized when needed by gamma radiation or ETO (ethylene oxide) to allow aseptic filling, for example to sterilize the port and pouch assembly after they are assembled.

The rigid body 10 is for example shaped from thermoplastic polymer. In particular, the body 10 may be polypropylene. Alternatively, the body 10 may be high density polyethylene.

Embodiments that can be combined are discussed below.

Figure 3:
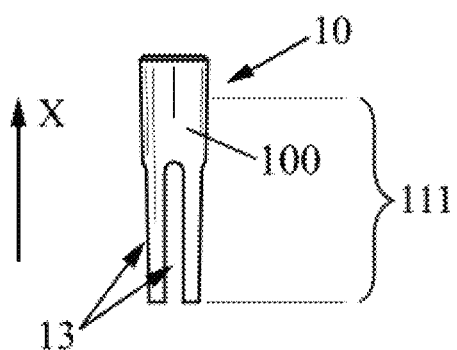
FIG. 3 illustrates a port with ribs.

In one embodiment illustrated in FIG. 3, the outer portion 111 of the rigid body 10 may comprise ribs 13 formed in the thickness of the wall 100, said ribs 13 being of elongate shape and oriented in a direction substantially parallel to direction X, said ribs 13 being formed in the outer portion 111 of the rigid body 10. Said ribs 13 will for example be formed in the outer surface of the wall 100 of the rigid body 10, within the thickness of the wall 100. Advantageously, the ribs 13 extend through the wall 100 along their entire length, meaning that the entire thickness of the wall may be pierced by the ribs 13. Alternatively, the ribs 13 may zigzag along their general direction of extension, as presented above.

Such ribs 13 allow better adhesion of the overmolding member 20 to the surface of the body 10.

Figure 4:
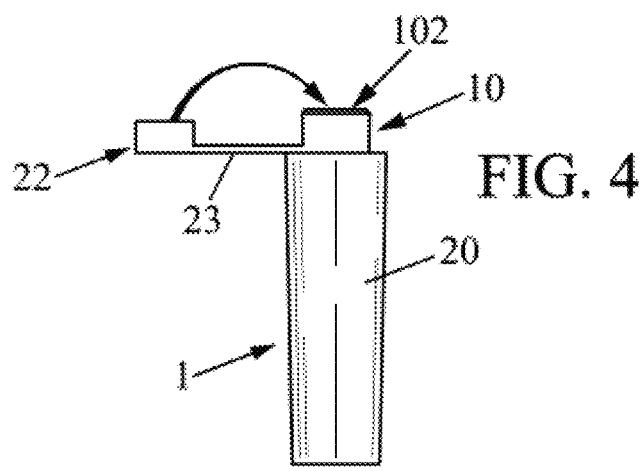
FIG. 4 is a side view illustrating a port with a cap.

In one embodiment illustrated in FIG. 4, the rigid body 10 comprises a cap member 22, the cap member 22 having dimensions suitable for sealing the outer end of the body 10. The cap member 22 is for example connected to the rigid body by a connector 23, the cap member 22, rigid body 10, and connector 23 being molded as one piece. The molding is such that the connector 23 extends radially from the side wall 100 below the outer end 102.

Alternatively, the overmolding member 20 may comprise a cap member 22, said cap member being integral with the sealing portion of the overmolding member, the cap member 22 having dimensions suitable for sealing the outer end 102 of the body 10. The cap member 22, the overmolding member 20, and a connector 23 connecting the cap member 22 to the sealing portion 21 are for example molded as one piece. The cap member 22 has for example dimensions suitable for insertion into the rigid body 10 through the outer end 102, having for example a frustoconical shape, and/or is compressible, which allows it to be inserted by force into the outer end 102 of the body 10 and close it. Alternatively, the cap member 22 has dimensions suitable for fitting around the rigid body 10 at its outer end 102, for example having a circular cross-section of a diameter greater than the diameter of the circular cross-section of the rigid body 10, so that the cap member 22 covers a portion of the wall 100 of the rigid body 10 at its outer end 102.

Figure 5:
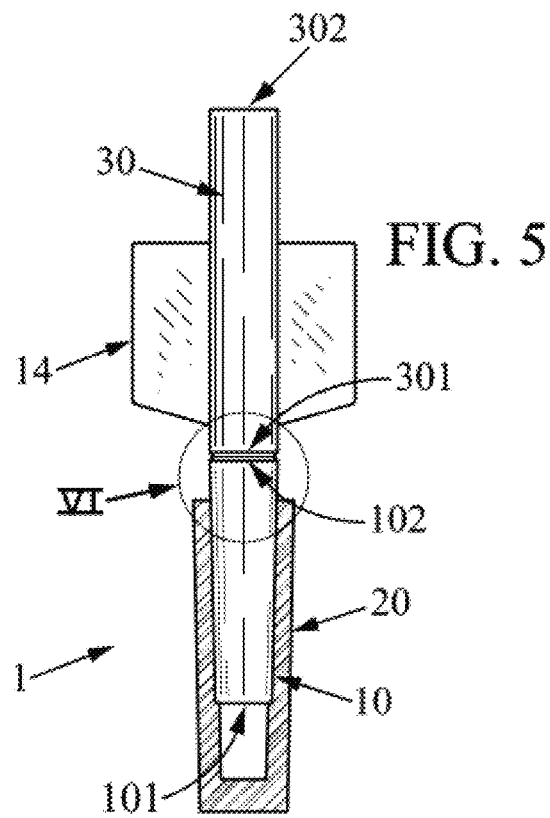
FIG. 5 is a view similar to FIG. 1 for a second embodiment of a port with a breakable portion and fins.

In one embodiment illustrated in FIG. 5, the rigid body 10 comprises an additional member forming a breakable portion 30, said breakable portion 30 comprising an outer end 302 and an inner end 301, the breakable portion 30 extending in direction (X) atop the rigid body 10 from the outer end 102 of the rigid body 10, defining a connection region 15 in the area where the outer end of the body 102 meets the inner end of the breakable portion 301. The outer end of the breakable portion 302 is sealed closed. It may be sealed in particular by ultrasonic welding.

Figure 6:
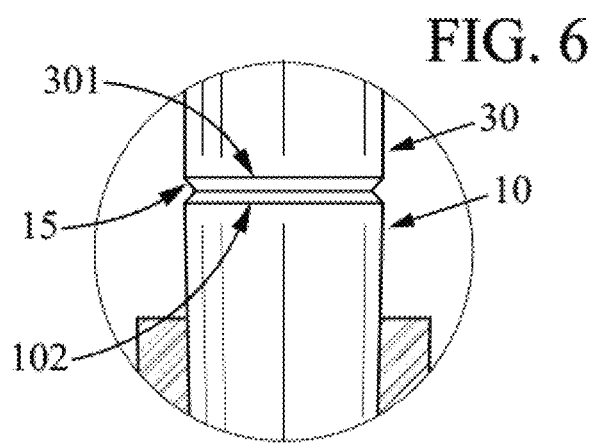
FIG. 6 is a close-up of FIG. 5 illustrating the connection region.

The rigid body 10 is, for example, molded with its breakable portion 30, the assembly of the rigid body 10 and its breakable portion 30 being weakened at the connection region 15 as shown in FIG. 6. The connection region 15 between the rigid body 10 and its breakable portion 30 is thus weakened, which facilitates breaking at this connection region when force is applied in a direction transverse to direction (X).

Such a breakable portion 30 allows eliminating any risk of contamination, impurity, or dust in the port 1 before its first use, the outer end 302 of the breakable portion being closed. The user can detach the breakable portion 30 from the rest of the rigid body 10 prior to its first use, the breakable portion 30 acting as evidence of tampering, meaning that as long as it is not removed, one can be certain that the port 1 has not been used. Ports comprising a breakable portion 30 can also be more easily transported without requiring particularly protective packaging.

In one advantageous embodiment, the breakable portion 30 may comprise fins 14, as illustrated in FIG. 5, suitable for gripping in order to detach the breakable portion 30 from the rigid body 10. Said fins 14 may for example be molded with the breakable portion 30.

The method for manufacturing such a port 1 will include the steps of providing a rigid body 10 as described above, as well as a system of molds 3 suitable for the manufacture of an overmolding member 20 made of elastomer thermoplastic, as well as a molding product 33.

The manufacture will consist of placing the mold system 3 so as to enable the manufacture of an overmolding member 20, enveloping the outer portion 111 of said body and the inner end surface of said body 101, molding said overmolding member 20, then removing the mold system 3.

Figure 7A:
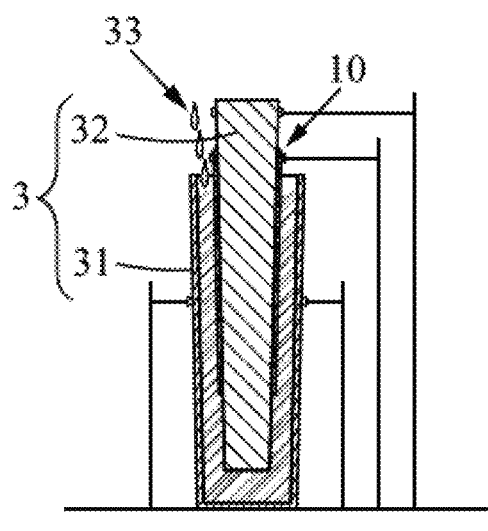
FIGS. 7a and 7b are schematic views illustrating various manufacturing steps of a method for creating a port.
Figure 7B:
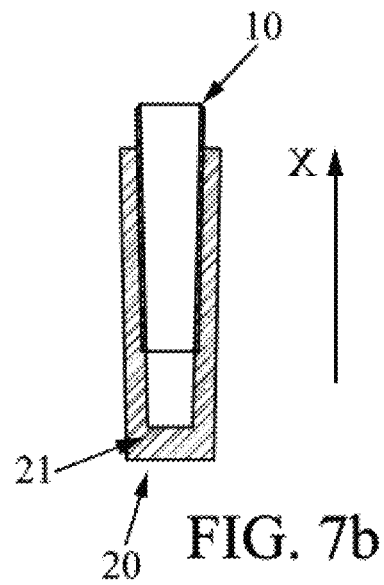

In one embodiment, the mold system 3 may comprise two molds, a first mold 31 suitable for surrounding the outer portion 111 of said body 10 and a second mold 32 suitable for insertion into the rigid body 10. The first mold 31 may for example be a cylinder of axis (X) and closed at one of its ends, into which the body 10 can be inserted, and the second mold 32 may be a cylinder of axis (X) and of slightly smaller diameter than the diameter of the annular body 10. As illustrated in FIG. 7a, the body 10 can be inserted at least partially into the first mold 31 and the second mold 32 can traverse the body 10 from one side to the other while extending through each of the ends of the body 10. The wall of the body 10 will be between the lateral surface of the first mold 31 and the lateral surface of the second mold 32, and the molding product 33 can be poured between the first and second molds 31, 32. A small amount of molding product may in particular be inserted between the lateral surface of the second mold 32 and the wall of the body 10. As illustrated in FIG. 7b, the mold system 3 will then be removed, releasing the port 1.

The overmolding member 20 will be partially inserted into the container 40 through the opening, then the wall of the container at its opening will be welded by a cold welding method, such as high frequency welding, to the adhesion portion of the overmolding member 20, by applying an electromagnetic field through the rigid body 10, the wall of the container at its opening, and the overmolding member 20, which will thus be welded by transfer of the electromagnetic field energy.

Ribs 13 formed in the rigid body 10 as described above will improve the welding of the pouch 40 to the surface of the overmolding member 20. In fact, the ribs will help to better distribute the current into the overmolding member 20 which is thus advantageously made malleable by the heating effect, improving the weld.

In the case of a port 1 comprising a breakable portion 30, the breakable portion will be detached from the rigid body 10 prior to insertion of the needle 50 into the outer end 102 of the rigid body 10.

The sterility of the port 1 can be guaranteed before its use in the dispensing system 2, for example by sterilization with gamma rays.

In the case of an EVA pouch, the assembly can therefore be easily sterilized.

Use may be made of a dispensing system 2 for dispensing content between the outside and the inside of a container 40 by means of a needle 50, by inserting a needle 50 into a port 1 previously assembled to said container 40.

After using the port 1 of the dispensing system 2, the needle 50 is removed, then the cap 22 is used to close off the chamber formed by the container at the port 1, ensuring a better seal.

Alternatively, the side wall 100 of the rigid body 10 may have a shoulder located under the outer end 102 and above the attachment of the connector 23 connecting the cap 22, the connector 23 extending radially from the side wall 100. The inside of the cap 22 has for example a groove to fit with the shoulder. This constitutes a closure that is tamper-proof or difficult to re-open without using enough force to damage the cap 22.

The invention claimed is:

1. A dispensing system for dispensing fluidic content, said system comprising:
    a container comprising a wall with an opening therein, the container defining an interior open volume configured to receive the fluidic content therein; and
    a port attached to the opening of the container and configured to be traversed by a needle configured to transfer the fluidic content between an inside of the container and an outside of the container, said port comprising:
        a rigid annular member extending in a longitudinal direction, said rigid annular member comprising a side wall surrounding a channel extending in the longitudinal direction between an inner end and an outer end of the rigid annular member and configured to receive the needle, said rigid annular member being open at the inner and outer ends to allow the needle to pass therethrough, and
        an overmolding member made of thermoplastic elastomer and disposed around the rigid annular member, the overmolding member comprising
            an annular body extending in the longitudinal direction from a proximal end portion affixed to the wall of the container to a distal end portion extending into the open volume of the container, the annular body comprising
                an inner surface directly contacting the side wall of the rigid annular member, and
                an outer surface having an adhesion portion that directly welds the outer surface at the proximal end portion of the annular body to the wall of the container at the opening, and
            a sealing portion integrally formed with the annular body at a lower end thereof, the sealing portion being configured to be traversed by the needle in a direction close to the longitudinal direction and configured to seal the overmolding member in a fluid-tight manner in the absence of the needle after withdrawal of the needle,
    wherein the overmolding member is configured to seal the channel in a fluid-tight manner in the absence of the needle after withdrawal of the needle.

2. The dispensing system according to claim 1, wherein the rigid annular member of the port is made of a thermoplastic polymer selected among polypropylene and high-density polyethylene.

3. The dispensing system according to claim 1, wherein the rigid annular member of the port comprises ribs formed in the thickness of the side wall, said ribs being elongated in a direction substantially parallel to the longitudinal direction.

4. The dispensing system according to claim 3, wherein the ribs either extend in a straight line or zigzag along the direction substantially parallel to the longitudinal direction.

5. The dispensing system according to claim 1, further comprising a cap selectively sealing the outer end of the rigid annular member.

6. The dispensing system according to claim 5, further comprising a connector connecting the cap to the rigid annular member,
    the cap, the rigid annular member, and connector being molded as one piece.

7. The dispensing system according to claim 1, wherein the rigid annular member of the port comprises a breakable portion connected to a remaining portion of the rigid annular member at a connection region, the breakable portion being sealed closed.

8. The dispensing system according to claim 7, wherein the rigid annular member is molded, said rigid annular member being weakened at the connection region to separate the breakable portion from the remaining portion of the rigid annular member.

9. The dispensing system according to claim 7, wherein the breakable portion comprises gripping fins.

10. The dispensing system according to claim 9, wherein said gripping fins are integrally molded to the breakable portion.

11. The dispensing system according to claim 1, wherein the container is a flexible pouch of plastic film configured to hold biopharmaceutical content.

12. The dispensing system according to claim 1, wherein the inner surface of the annular body of the overmolding member is in direct contact with the side wall of the rigid annular member on an outer longitudinal portion of rigid annular body smaller than its length such that a free space is disposed between the sealing portion of the overmolding element and the inner end of the rigid annular member.

13. The dispensing system according to claim 3, wherein the ribs extend through the entire thickness of the side wall.

14. The dispensing system according to claim 3, wherein the ribs extend only on a lower portion of the side wall.

15. The dispensing system according to claim 5, wherein the cap is configured to selectively cover a portion of the side wall of the rigid annular member.

16. The dispensing system according to claim 5, wherein the cap is configured to be inserted into the outer end of the rigid annular member.

17. A port configured to attach directly to a wall of a container at an opening thereof and configured to be traversed by a needle configured to transfer a fluidic content between an inside of the container and an outside of the container, the container defining an interior open volume configured to receive the fluidic content therein, the port comprising:
   a rigid annular member extending in a longitudinal direction, the rigid annular member comprising a side wall surrounding a channel extending in the longitudinal direction between an inner end and an outer end and configured to receive the needle, the channel being configured to receive the needle, the rigid annular member being open at the inner and outer ends to allow the needle to pass therethrough; and
   an overmolding member made of thermoplastic elastomer and disposed around the rigid annular member, the overmolding member comprising
      an annular body extending in the longitudinal direction from a proximal end portion affixed to the wall of the container to a distal end portion extending into the open volume of the container, the annular body comprising
         an inner surface directly contacting the side wall of the rigid annular member, and
         an outer surface having an adhesion portion configured to directly weld the outer surface at the proximal end portion of the annular body to the wall of the container at the opening, and
      a sealing portion integrally formed with the annular body at a lower end thereof, the sealing portion being configured to be traversed by the needle in a direction close to the longitudinal direction and configured to seal the overmolding member in a fluid-tight manner in an absence of the needle after withdrawal of the needle,
   wherein the sealing portion is free at a bottom end thereof, and
   wherein the overmolding member is configured to seal the channel in a fluid-tight manner in the absence of the needle after withdrawal of the needle.

18. The port according to claim 17, wherein the inner surface of the annular body of the overmolding member is in direct contact with the side wall of the rigid annular member on an outer longitudinal portion of rigid annular body smaller than its length such that a free space is disposed between the sealing portion of the overmolding element and the inner end of the rigid annular member.

* * * * *